United States Patent
Shirai et al.

(10) Patent No.: US 11,918,337 B2
(45) Date of Patent: Mar. 5, 2024

(54) MAGNETIC RESONANCE IMAGING APPARATUS, NOISE REDUCTION METHOD AND IMAGE PROCESSING APPARATUS

(71) Applicant: FUJIFILM Healthcare Corporation, Kashiwa (JP)

(72) Inventors: Toru Shirai, Chiba (JP); Suguru Yokosawa, Chiba (JP); Yukio Kaneko, Chiba (JP); Atsuro Suzuki, Chiba (JP); Tomoki Amemiya, Chiba (JP)

(73) Assignee: FUJIFILM Healthcare Corporation, Chiba (JP)

(*) Notice: Subject to any disclaimer, the term of this patent is extended or adjusted under 35 U.S.C. 154(b) by 25 days.

(21) Appl. No.: 17/832,772

(22) Filed: Jun. 6, 2022

(65) Prior Publication Data
US 2022/0395188 A1 Dec. 15, 2022

(30) Foreign Application Priority Data
Jun. 15, 2021 (JP) .................. 2021-099577

(51) Int. Cl.
*A61B 5/055* (2006.01)
*G01R 33/3415* (2006.01)
(Continued)

(52) U.S. Cl.
CPC .......... *A61B 5/055* (2013.01); *G01R 33/3415* (2013.01); *G01R 33/5608* (2013.01);
(Continued)

(58) Field of Classification Search
None
See application file for complete search history.

(56) References Cited

U.S. PATENT DOCUMENTS

| 2019/0086496 A1* | 3/2019 | Moeller | G06T 11/005 |
| 2021/0290191 A1* | 9/2021 | Qi | A61B 6/5211 |

FOREIGN PATENT DOCUMENTS

| JP | 2020-103890 | 7/2020 |
| JP | 6762284 | 9/2020 |

OTHER PUBLICATIONS

Pruessmann K.P., et al., "SENSE: Sensitivity Encoding for Fast MRI", Magnetic Resonance in Medicine, vol. 42, pp. 952-962, 1999.

(Continued)

*Primary Examiner* — Douglas X Rodriguez
(74) *Attorney, Agent, or Firm* — Paul Teng

(57) ABSTRACT

The present invention is to perform appropriate noise reduction processing on an image having different signal levels or noise levels depending on an imaging condition or a reconstruction condition. A magnetic resonance imaging apparatus according to the invention includes: a measurement unit that receives a nuclear magnetic resonance signal generated in a subject by a receiving coil; an image reconstruction unit that processes the nuclear magnetic resonance signal received by the receiving coil and reconstructs an image of the subject; an SNR spatial distribution calculation unit that calculates spatial distribution of a signal-to-noise ratio of the image using spatial distribution of a noise level and spatial distribution of the signal of the image; and a noise reduction unit that reduces noise from the image based on the spatial distribution of the signal-to-noise ratio.

18 Claims, 11 Drawing Sheets

(51) Int. Cl.
- G01R 33/56    (2006.01)
- G01R 33/561   (2006.01)
- G06T 7/00     (2017.01)

(52) U.S. Cl.
CPC ........ *G01R 33/5611* (2013.01); *G06T 7/0012* (2013.01); *G06T 2207/10088* (2013.01)

(56) References Cited

OTHER PUBLICATIONS

Japanese official action dated Dec. 12, 2023 (and English translation thereof) in connection with Japanese Patent Application No. 2021-099577.

Scott B. Reeder, "Measurement of Signal-to-Noise Ratio and Parallel Imaging", Parallel Imaging in Clinical MR Applications, pp. 49-61 (2007).

* cited by examiner

HISTOGRAM OF ABSOLUTE VALUE IMAGE
(3T HUMAN HEAD T2WI)

HISTOGRAM OF ABSOLUTE VALUE IMAGE
(Shepp-logan)

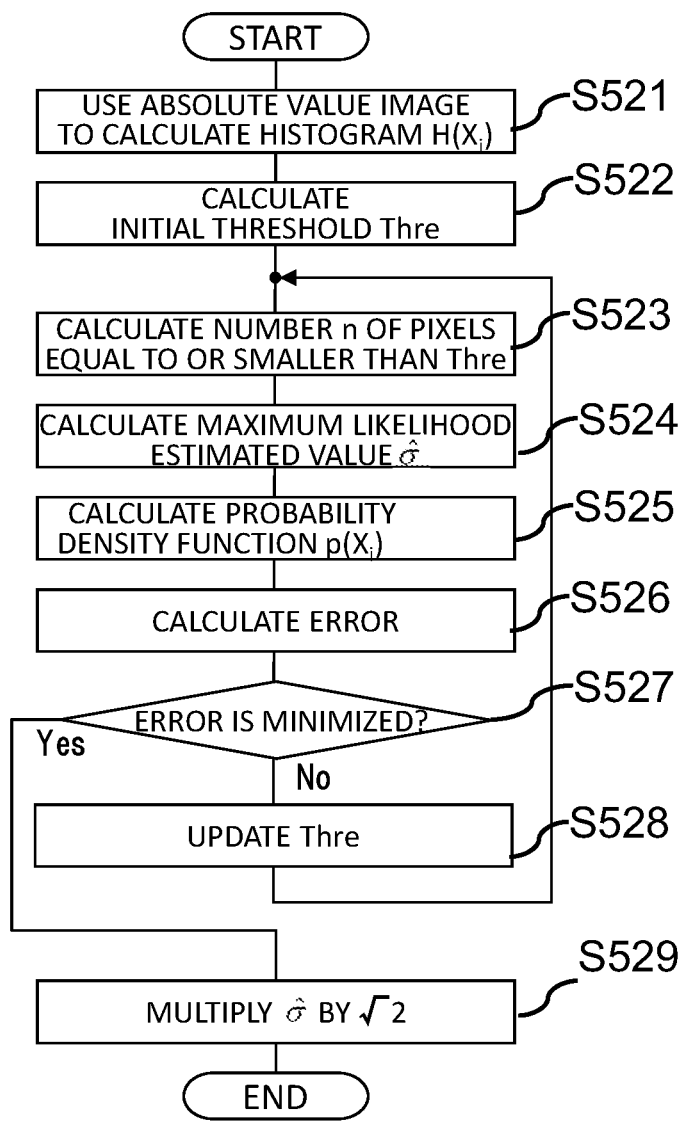

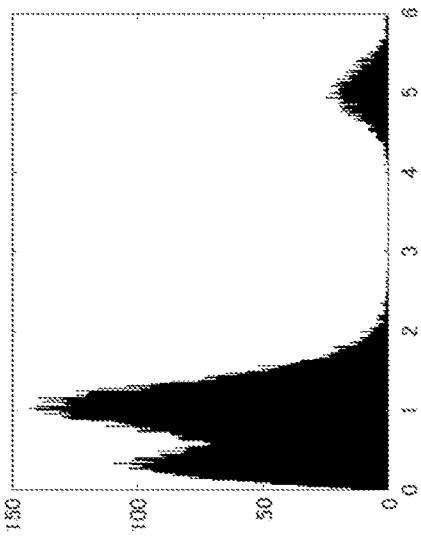
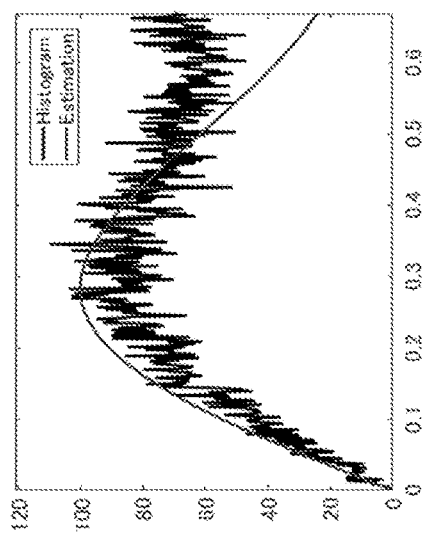
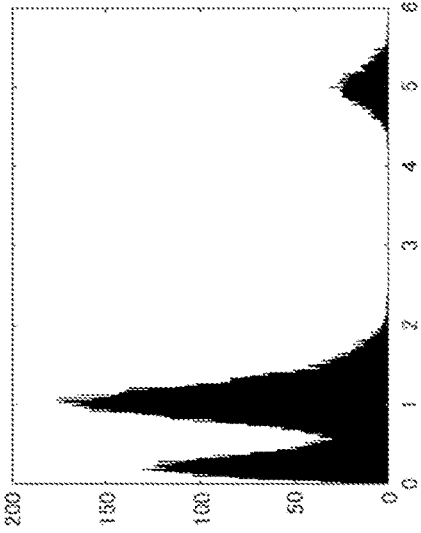
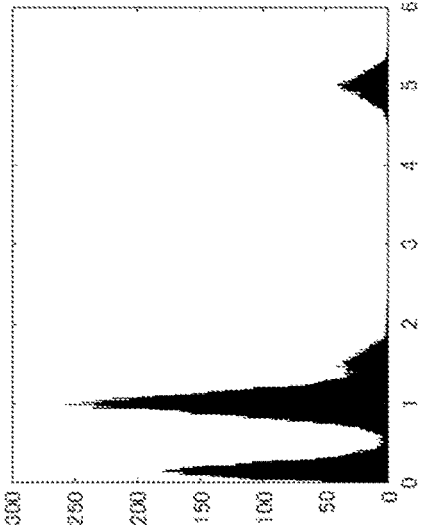

MAGNETIC RESONANCE IMAGING APPARATUS, NOISE REDUCTION METHOD AND IMAGE PROCESSING APPARATUS

BACKGROUND OF THE INVENTION

1. Technical Field

The present invention relates to an image processing technique for an image acquired by a medical imaging apparatus, and particularly to a noise reduction technique for an image acquired by a magnetic resonance imaging apparatus (hereinafter, referred to as an MRI apparatus).

2. Related Art

An image acquired by the medical imaging apparatus includes various noises due to accuracy of the apparatus, imaging conditions, factors on examination target side, and the like. Many techniques for reducing these noises according to types and causes of the noises have been developed.

For example, Gaussian noise, spike noise, and the like are reduced by replacing a pixel value with an average value, a median value, a weighted average value, or the like for each local region formed of a small number of pixels. Specifically, processing for reducing these noises is implemented by various filters such as a box filter, a median filter, a Gaussian filter, a bilateral filter, and a non-local means (NLM) filter, and noise reduction effects and edge preserving effects are different depending on filter types.

In addition, there are a noise reduction method using sparse transform such as wavelet transform and curvelet transform, and a noise reduction method using machine learning (noise reduction model) in recent years.

In MRI, a diagnostic image is usually calculated by reconstructing an image acquired from a plurality of receiving coils. For this reason, noise imposed on an MRI image changes depending on arrangement of the receiving coils and an image reconstruction method in addition to the imaging conditions, and cannot be appropriately reduced by noise reduction methods in the related art. On the other hand, a method for analyzing noise in an MRI image and effectively reducing the noise based on the analysis result has been proposed (e.g., Japanese Patent No. 6762284, JP-A-2020-103890). Regarding an image reconstructed by a parallel imaging method, a technique disclosed in Japanese Patent No. 6762284 proposes that based on a fact that there is noise correlation between an image in a state where spatially overlapping signals are not separated (pre-separation image) and an image after signal separation (post-separation image), the noise correlation is added to a constraint condition of noise reduction processing.

In the method disclosed in JP-A-2020-103890, in images acquired from a plurality of receiving coils, a degree of noise reduction is first adjusted based on a noise index value of each coil image, and noise is reduced for each coil image. Thereafter, coil images after noise reduction are synthesized to calculate a diagnostic image. As to the noise index value, it is disclosed that a signal-to-noise ratio (SNR) is derived by performing imaging a plurality of times under different RF conditions, and the SNR is used as the noise index value.

SUMMARY OF THE INVENTION

It is known that, when a parallel imaging method (Pruessmann K P et al., "SENSE: Sensitivity Encoding for Fast MRI", Magnetic Resonance in Medicine, vol. 42, pp. 952-962, 1999) (Non-patent Literature 1) for shortening an imaging time by using a plurality of receiving coils is applied, a SNR is inversely proportional to an index called a geometry factor (g factor). Therefore, noise spatially changes in accordance with the g factor at the time of parallel imaging reconstruction. Even if the technique disclosed in JP-A-2020-103890 is applied to reduce noise from the coil images before parallel imaging reconstruction, the SNR degrades in accordance with the g factor after parallel imaging reconstruction, and noise cannot be appropriately reduced.

In addition, the technique disclosed in JP-A-2020-103890 also has a problem that, a plurality of times of imaging are required to calculate the SNR since a plurality of times of imaging under different RF conditions are performed to calculate the SNR and derive the index.

An object of the invention is to effectively reduce noise from an image having various noise levels due to different imaging conditions, to obtain an image in which noise is reduced even from an image obtained by synthesizing data of a plurality of receiving coils, and to reduce imaging and calculation for noise reduction.

In order to solve the above problems, the invention obtains SNR spatial distribution using spatial distribution of a noise level of an image and spatial distribution of signal values, and reduces noise that reflects the SNR spatial distribution.

That is, a magnetic resonance imaging apparatus according to the invention includes: a measurement unit configured to receive a nuclear magnetic resonance signal generated in a subject by a receiving coil; an image reconstruction unit configured to process the nuclear magnetic resonance signal received by the receiving coil and reconstruct an image of the subject; an SNR spatial distribution calculation unit configured to calculate spatial distribution of a signal-to-noise ratio of the image using spatial distribution of the noise level and spatial distribution of the signal of the image; and a noise reduction unit configured to reduce noise from the image based on the spatial distribution of the signal-to-noise ratio.

A noise reduction method according to the invention is a method of reducing noise from an image acquired by a magnetic resonance imaging apparatus, the noise reduction method including steps of: calculating spatial distribution of a signal-to-noise ratio; and reducing noise from the image based on the spatial distribution of the signal-to-noise ratio. The step of calculating the spatial distribution of the signal-to-noise ratio includes steps of: calculating a noise level of the image; calculating spatial distribution of the noise of the image; and calculating spatial distribution of a signal of the image. The spatial distribution of the signal-to-noise ratio is calculated using the noise level, the spatial distribution of the noise, and the spatial distribution of the signal.

Further, an image processing apparatus according to the invention is configured to reduce noise from an image acquired by a medical imaging apparatus. The image processing apparatus includes: an SNR spatial distribution calculation unit configured to calculate spatial distribution of a signal-to-noise ratio based on the image to be subjected to noise processing; and a noise reduction unit configured to reduce noise from the image based on the spatial distribution of the signal-to-noise ratio.

According to the invention, it is possible to effectively reduce noise from an image having different signal levels and noise levels depending on imaging conditions by performing noise reduction processing on the image based on spatial distribution of a signal-to-noise ratio calculated from the image. Further, according to the invention, an imaging method using a plurality of receiving coils can also reduce noise that may occur at the time of synthesis by applying noise reduction to the synthesized image.

BRIEF DESCRIPTION OF THE DRAWINGS

FIG. 7 is a diagram showing noise level calculation processing in FIG. 5 in detail.

FIGS. 9A to 9C are diagrams showing effects of the first embodiment.

DESCRIPTION OF EMBODIMENTS

Hereinafter, an embodiment of an MRI apparatus according to the invention will be described.

[Outline of MRI Apparatus]

Figure 1:
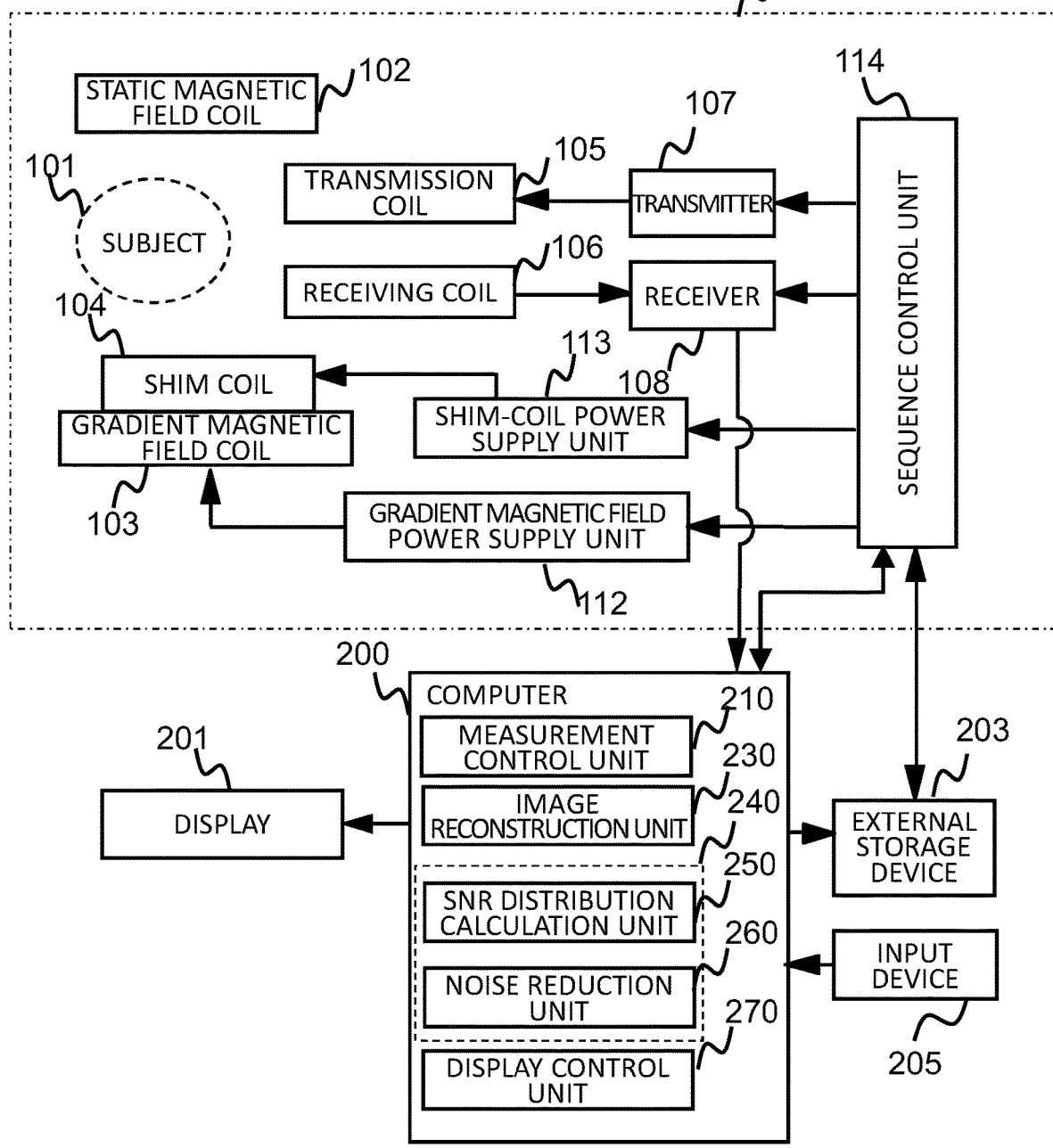
FIG. 1 is an overall block diagram showing an embodiment of an MRI apparatus according to the invention.

As shown in FIG. 1, the MRI apparatus of the present embodiment is roughly divided into a measurement unit 100 that measures a nuclear magnetic resonance signal generated from a subject 101, and a computer 200 that controls the measurement unit 100 and performs image reconstruction, correction, and other calculations using the nuclear magnetic resonance signal measured by the measurement unit 100.

The measurement unit 100 includes a static magnetic field coil 102 that generates a static magnetic field in space placed with the subject 101, a transmission unit (105, 107) that transmits a high-frequency magnetic field pulse to the subject 101 disposed in the static magnetic field, a reception unit (106, 108) that receives the nuclear magnetic resonance signal generated by the subject, and a gradient magnetic field coil 103 that applies a magnetic field gradient to the static magnetic field generated by the static magnetic field coil 102 in order to provide position information for the nuclear magnetic resonance signal.

The static magnetic field coil 102 includes a normal conducting or superconducting static magnetic field coil, a static magnetic field generating magnet, and the like. A vertical magnetic field type, a horizontal magnetic field type, and the like depending on a direction of the generated static magnetic field are in existence, and a shape of the coil and an appearance of the entire apparatus are different depending on the type. The present embodiment is applicable to any type of MRI apparatus.

The transmission unit includes a transmission high-frequency coil 105 (hereinafter, simply referred to as transmission coil) that transmits a high-frequency magnetic field to a measurement region of the subject 101, and a transmitter 107 including a high-frequency oscillator, an amplifier, and the like. The reception unit includes a reception high-frequency coil 106 (hereinafter, simply referred to as receiving coil) that receives the nuclear magnetic resonance signal generated from the subject 101, and a receiver 108 including a quadrature detection circuit, an A/D converter, and the like. In the present embodiment, the receiving coil includes a plurality of channels (small receiving coils), and each of the channels is coupled to a quadrature detection circuit and an A/D converter that constitute the receiver 108. The nuclear magnetic resonance signal received by the receiver 108 is passed to the computer 200 as a complex digital signal. The receiving coil 106 is composed of a receiving coil in which a plurality of small coils are combined, and the nuclear magnetic resonance signal received by each receiving coil is passed to the computer 200 for synthesis at the time of image reconstruction.

The gradient magnetic field coil 103 includes three sets of gradient magnetic field coils that apply gradient magnetic fields in an x direction, a y direction, and a z direction respectively, and each set of gradient magnetic field coil is coupled to a gradient magnetic field power supply unit 112. The MRI apparatus may further include a shim coil 104 for adjusting static magnetic field distribution and a shim-coil power supply unit 113 for driving the shim coil 104.

The measurement unit 100 further includes a sequence control device 114 that controls operations of the measurement unit 100. The sequence control device 114 controls operations of the gradient magnetic field power supply unit 112, the transmitter 107, and the receiver 108, and controls application of the gradient magnetic field and the high-frequency magnetic field and a reception timing of the nuclear magnetic resonance signal. A time chart of the control is referred to as a pulse sequence, is set in advance according to the measurement, and is stored in a storage device or the like included in the computer 200 to be described later.

The computer 200 controls operations of the entire MRI apparatus 10 and performs various computation processing on the received nuclear magnetic resonance signal. The computer 200 is an information processing device including a CPU, a memory, a storage device, and the like, and is coupled to a display 201, an external storage device 203, an input device 205, and the like.

The display 201 is an interface for displaying a result obtained by computation processing and the like to an operator. The input device 205 is an interface for the operator to input conditions, parameters, and the like necessary for measurement and computation processing performed in the present embodiment. A user can input measurement parameters such as a multiple speed number in a parallel imaging (PI) method, for example, via the input device 205. The external storage device 203 holds data used for various computation processing executed by the computer 200, data obtained by the computation processing, input conditions and parameters, and the like together with the storage device inside the computer 200.

In the present embodiment, the computer 200 performs image synthesis using sensitivity distribution of the receiving coil, noise reduction processing, and the like, as a function of image processing. Therefore, as shown in FIG. 1, the computer 200 includes functional units such as a measurement control unit 210, an image reconstruction unit 230, a noise processing unit 240, and a display control unit 270. The noise processing unit 240 has a function of performing noise reduction processing on an image generated by the image reconstruction unit 230, and includes an SNR distribution calculation unit 250 and a noise reduction unit 260.

Functions of these units can be implemented as software embedded in the computer 200, and are implemented by the CPU loading a program (software) held by the storage device into the memory and executing the program. Various types of data used for processing of the functions and various types of data generated during the processing are stored in the storage device or the external storage device 203. Some of the various functions implemented by the computer 200 may be implemented by hardware such as an application specific integrated circuit (ASIC) or a field-programmable gate array (FPGA).

Figure 2:
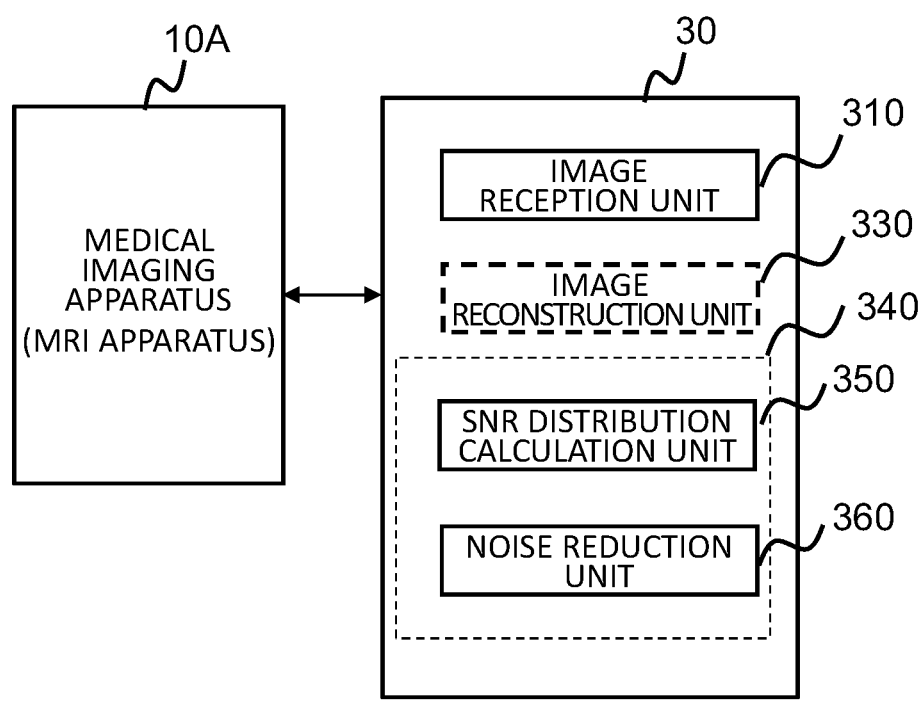
FIG. 2 is a functional block diagram of an image processing apparatus according to the invention.

As shown in FIG. 2, the function related to image processing among the functions implemented by the computer may be implemented by an image processing apparatus 30, which is independent of the MRI apparatus 10 and capable of transmitting and receiving data to and from the MRI apparatus 10.

The image processing apparatus 30 includes an image reception unit 310 that receives an image from a medical imaging apparatus 10A, and a noise processing unit 340 including an SNR distribution calculation unit 350 and a noise reduction unit 360 similarly to the computer 200 of the MRI apparatus 10 shown in FIG. 1. The medical imaging apparatus 10A is not limited to the MRI apparatus, and may be a CT apparatus, or an ultrasonic imaging apparatus, or even a database that stores various medical images. Although not essential, the image processing apparatus 30 may include an image reconstruction unit 330 that reconstructs an image based on an image received from the medical imaging apparatus 10A or measurement data.

Figure 3:
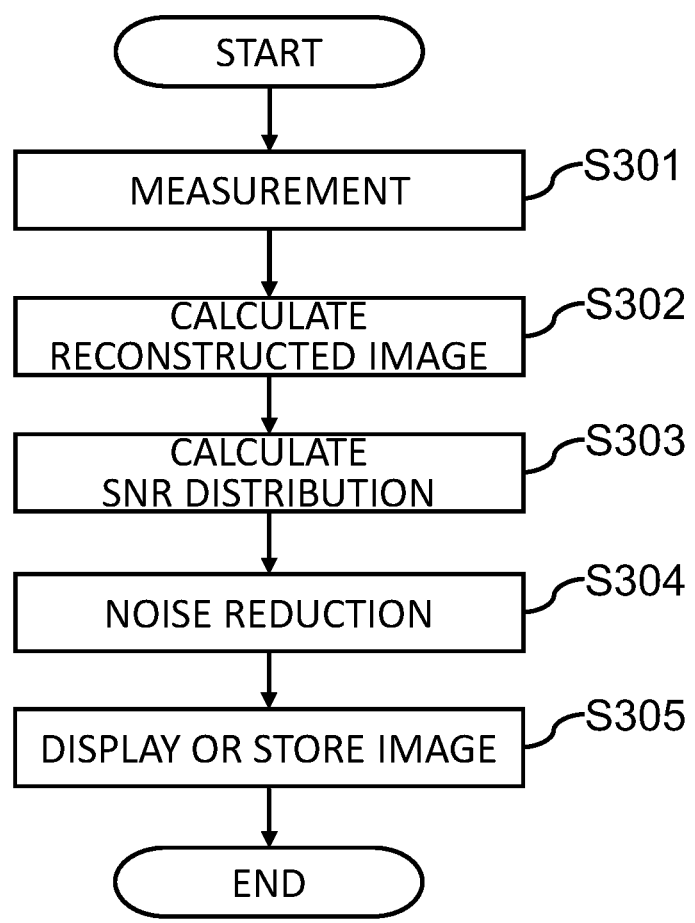
FIG. 3 is a diagram showing an outline of processing performed by the MRI apparatus in FIG. 1.

Next, an outline of operations of the MRI apparatus (mainly, the computer 200) and the image processing apparatus according to the present embodiment will be described. Functions of all the units of the image processing apparatus 30 are basically the same as an image processing function of the MRI apparatus, and each unit of the MRI apparatus will be referred to as follows. FIG. 3 shows a flow of operations.

[Measurement: S301]

First, setting of an imaging sequence and an imaging condition by the user is received via the input device 205. The imaging sequence is not particularly limited, for example, the PI method using a high-speed pulse sequence such as 2D-RSSG (RF-spoiled-steady-state acquisition with rewound gradient-echo) sequence is selected and set. The imaging condition includes parameters (repetition time TR and echo time TE) of the imaging sequence, and a reduction factor of sampled k-space data (R-factor) when sparse measurement in a k-space is performed. In a case of simultaneous excitation of a plurality of slices, setting of the number of slices is included. When the imaging condition and the like are set as an examination protocol, the condition and the like set in the examination protocol are read.

The measurement control unit 210 operates the sequence control device 114 in accordance with the pulse sequence set based on the parameters input by the user, and measures the nuclear magnetic resonance signal (echo signal) under a predetermined condition. The sequence control device 114 controls each unit of the MRI apparatus 10 in accordance with instructions from the measurement control unit 210, and receives the nuclear magnetic resonance signal by the receiving coil. When the receiving coil is a multi-channel coil including a plurality of receiving coils, k-space data is collected for each channel.

[Image Reconstruction: S302]

The image reconstruction unit 230 performs computation such as Fourier transform on the k-space data to reconstruct an image. In the case of the parallel imaging (PI) method, spatially overlapping signals are separated using the k-space data for each receiving coil and the sensitivity distribution of the plurality of receiving coils, and images at spatially different positions are created and synthesized. In a case of a compressed sensing (CS) method, iterative computation including L1 norm minimization is performed on randomly sampled k-space data to reconstruct the image.

[S303, S304]

Next, the noise processing unit 240 performs processing for reducing noise included in the reconstructed image.

Noise reduction is implemented by performing iterative computation so as to minimize noise under a predetermined constraint condition, similarly to a known nonlinear filter including total variation regularization or sparse regularization. The present embodiment reflects SNR spatial distribution of the image in the constraint condition to perform the iterative computation. Therefore, spatial distribution of a signal level of the image, the noise level and spatial distribution thereof are calculated for the image to be subjected to noise reduction, and the SNR spatial distribution is calculated using these amounts (S303). Thereafter, noise reduction using the SNR spatial distribution is performed (S304).

The image after noise reduction is stored in the storage device 203 or displayed on the display 201 as necessary (S305).

According to the present embodiment, even when the image has different signal levels and noise levels depending on imaging conditions, it is possible to reduce noise based on SNR spatial distribution with high accuracy by reducing noise based on the SNR spatial distribution calculated from the signal level and the noise level of the image. In addition, it is also possible to perform highly accurate noise reduction on an image reconstructed from spatially overlapping signals by the PI method or the like or an image after synthesis.

Hereinafter, embodiments of specific processing of the noise processing unit will be described. The outline of the MRI apparatus shown in FIG. 1 and an outline of processing shown in FIG. 3 are common to the following embodiments and will be referred to as appropriate.

First Embodiment

In the present embodiment, noise of an image obtained by high-speed imaging using a plurality of receiving coils is reduced. When the imaging method is a SENSE method, a target is a synthesized image. The synthesized image is obtained by synthesizing the image of each receiving coil after unfolding aliasing generated in the image of each receiving coil by matrix computation using the image reconstructed by each receiving coil and sensitivity information of each receiving coil.

Figure 4:
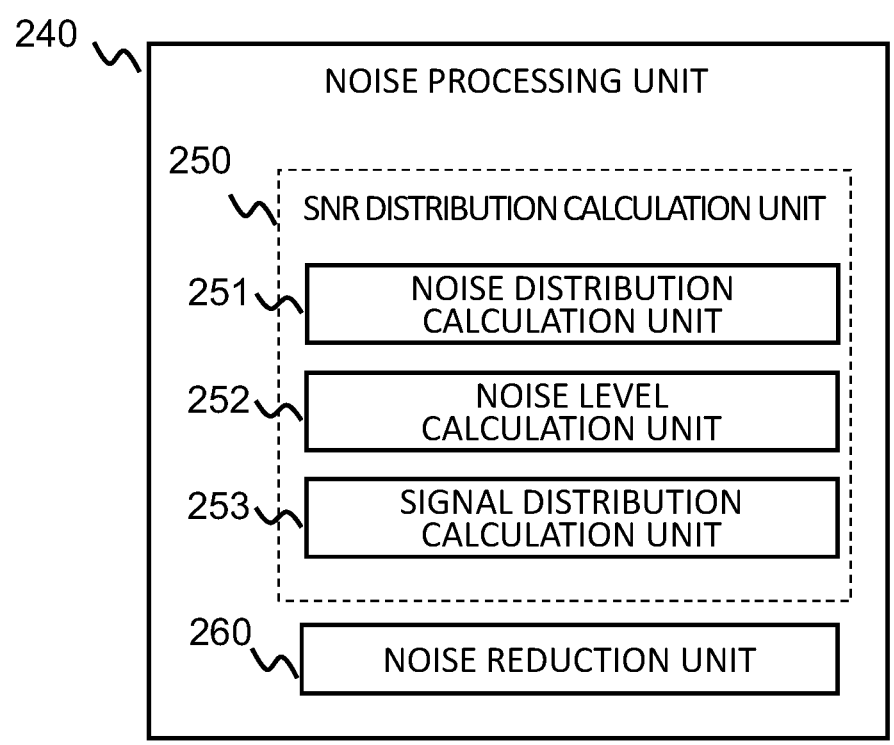
FIG. 4 is a functional block diagram of a noise processing unit according to a first embodiment.

A configuration of the noise processing unit 240 according to the present embodiment is shown in FIG. 4. As shown in FIG. 4, the noise processing unit 240 includes the SNR distribution calculation unit 250 and the noise reduction unit 260. The SNR distribution calculation unit 250 includes a noise distribution calculation unit 251, a noise level calculation unit 252, and a signal distribution calculation unit 253.

Figure 5:
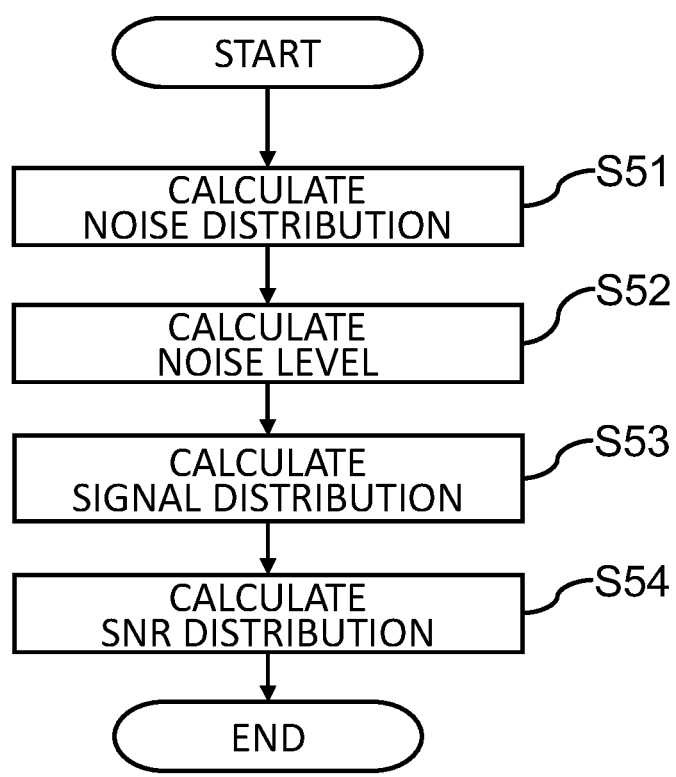
FIG. 5 is a diagram showing a flow of noise processing according to the first embodiment.

As shown in FIG. 5, in the noise processing (FIG. 3: S303) of the present embodiment with such a configuration, spatial distribution of noise is calculated based on a g factor of the receiving coil (S51), the noise level is calculated based on a histogram of the image (S52), and spatial distribution of the signal (excluding noise) is calculated using information of spatial distribution of the noise level (S53). The SNR spatial distribution is calculated based on the spatial distribution of noise and the spatial distribution of the signal (S54), and is used for noise reduction computation (FIG. 3: S304).

Hereinafter, each processing will be described in detail.

[Noise Distribution Calculation: S51]

The noise distribution calculation unit 251 calculates the spatial distribution of noise by obtaining a reciprocal of the g factor of the receiving coil. The g factor is a value that changes depending on the number and arrangement of the small receiving coils constituting the receiving coil, reduction factor of sampled k-space data (R-factor) of the PI method, and the like, and can be obtained in advance using the sensitivity distribution of the receiving coil and a correlation matrix of noise between receptions.

Here, the g factor can be calculated by an equation described in Non-patent Literature 1. When a receiving coil sensitivity matrix is S, a complex transpose matrix of the receiving coil sensitivity matrix is $S^H$, a noise correlation matrix is $\Psi$, and diag [A] is an operator for extracting diagonal element vectors of a matrix A, the g factor is expressed by the following Equation (1).

$$g = \sqrt{\text{diag}[(S^H \Psi^{-1} S)^{-1}] \text{diag}[S^H \Psi^{-1} S]} \qquad (1)$$

[Noise Level Calculation: S52]

In noise level calculation, a standard deviation (SD) of noise is calculated as a noise level by using a fact that a histogram of noise of an absolute value image follows the Rayleigh distribution.

Figure 6A:
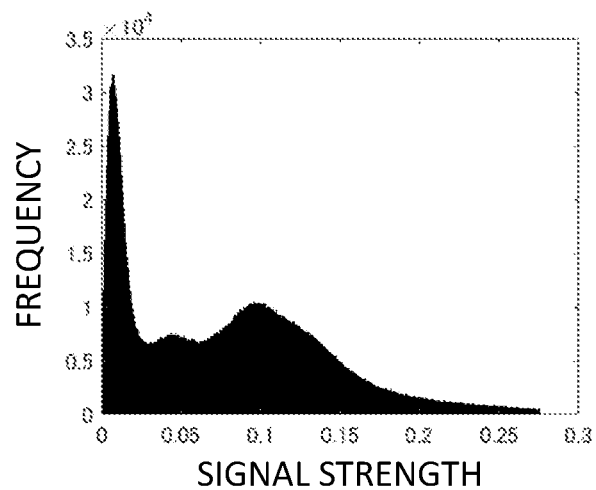
FIGS. 6A and 6B are diagrams showing examples of a histogram used in noise level calculation.

An example of the histogram of the absolute value image of a human head image (T2WI) is shown in FIG. 6A. As shown in FIG. 6A, an original image signal shows Gaussian distribution in the histogram. Alternatively, the noise has a peak in a region of low signal values, and the SD of noise follows the Rayleigh distribution of a parameter G when the SD of noise of a real image and an imaginary image is $\sigma$ respectively. The Rayleigh distribution can be expressed by the following Equation (2), and a mode thereof matches $\sigma$.

$$p(x) = \frac{x}{\sigma^2} \exp\left(-\frac{x^2}{2\sigma^2}\right) \qquad (2)$$

x: probability variable (0<x)

Assuming that a maximum likelihood estimated value of the mode $\sigma$ is $\hat{\sigma}$hat, $\hat{\sigma}$hat can be calculated by the following Equation (3).

$$\hat{\sigma} = \sqrt{\frac{1}{2n} \sum_{i=1}^{n} X_i^2} \qquad (3)$$

$X_i$: observed value of probability variable
n: number of pixels in region to be processed $\hat{\sigma} = \sigma hat$ Therefore, SD of complex noise can be calculated by obtaining σhat as the smallest difference (root mean square error: RMSE) between the histogram of the absolute value image and the Rayleigh distribution calculated from the maximum likelihood estimated value σhat, and multiplying the σhat by $\sqrt{2}$.

Figure 6B:
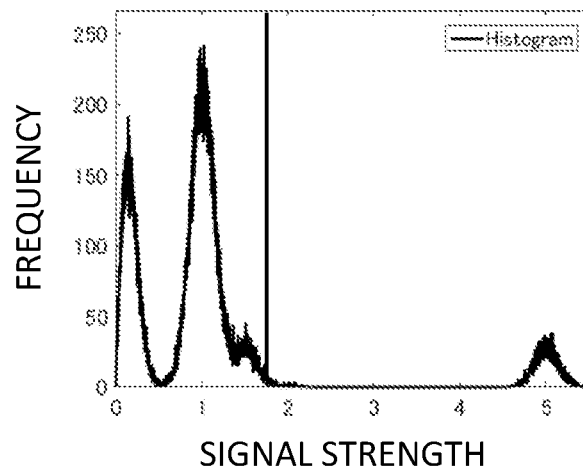

FIG. 7 shows a specific processing flow performed by the noise level calculation unit 252. First, a complex image is converted into an absolute value image, and the absolute value image is multiplied by the reciprocal of the g factor calculated in S51 to create a histogram (S521). Here, the spatial distribution of noise caused by parallel imaging is corrected by multiplying the reciprocal of the g factor (g factor map), and the SD (noise level) of uniform noise is obtained. As an example of the histogram created in this manner, a histogram H (SNR=5, noise SD=0.2) of an absolute value image of a Shepp-logan phantom is shown in FIG. 6B. When the number of bins of the histogram is set as N bins, the histogram H is denoted by $H(X_{nbin})$ ($X_{nbin}$ is a signal value of the n-th bin).

Next, a threshold (initial threshold) Thre of the histogram is calculated by a discriminant analysis method (S522). Then, the number n of pixels equal to or smaller than the threshold Thre and larger than 0 is calculated (S523). The maximum likelihood estimated value σhat is calculated based on the pixel value of the pixels (n pixels) equal to or smaller than the threshold Thre and larger than 0 by using the above Equation (2) (S524).

Next, a probability density function p(nbin) of the Rayleigh distribution is calculated by Equation (4) (S525).

$$p(X_{nbin}) = n \frac{p_0(X_{nbin})}{\sum_{i=1}^{n} p_0(X_{nbin})} \qquad (4)$$

where $$p_0(X_{nbin}) = \frac{X_{nbin}}{\hat{\sigma}^2} \exp\left(-\frac{X_{nbin}^2}{\hat{\sigma}^2}\right)$$

An error E between the calculated probability density function p(nbin) and the histogram H ($X_{nbin}$) is calculated by Equation (5) (S526), and steps of S523 to S526 are repeated while updating the threshold Thre (S528) until the error E is minimized (S527).

$$E = \sqrt{\frac{\sum_{i=1}^{n} |p(X_{nbin}) - H(X_{nbin})|^2}{n}} \qquad (5)$$

The maximum likelihood estimated value σhat when the error E is minimized is set as the mode σ of the Rayleigh distribution. When the error E is not a minimum value, the threshold Thre is reduced by Equation (6).

Thre=Thre−α·Thre  (6)

In Equation (6), a coefficient α is a ratio at which the threshold gradually decreases, for example, α=0.1, and thus Thre after update is about 90% of Thre before update. When the error decreases due to this update, the update is repeated, and when the error increases, the σhat calculated from Thre before update is set as the maximum likelihood estimated value.

When the maximum likelihood estimated value σhat in which the error is minimized is finally determined, the maximum likelihood estimated value σhat is set as the mode G of the Rayleigh distribution and multiplied by $\sqrt{2}$ (S529). That is, a noise level of the complex noise (noise SD) is calculated.

Spatial distribution of the noise level is obtained for the image to be processed by multiplying the calculated noise level by the g factor map (i.e., a relative noise SD).

[Signal Distribution Calculation: S53]

The signal distribution calculation unit 253 obtains spatial distribution of the signal from strength distribution calculated from an absolute value of the complex image to be processed.

[SNR Distribution Calculation: S54]

The SNR distribution calculation unit 250 uses the spatial distribution of signals calculated in S53 and the spatial distribution of the noise level calculated in S52 to calculate the SNR spatial distribution.

With processing S51 to S54 as described above, SNR distribution calculation processing S303 of FIG. 3 is completed.

[Noise Reduction: S304]

The noise reduction unit 260 performs noise reduction processing by the iterative computation (iterative processing). In the noise reduction processing, in addition to a constraint condition that an image before noise reduction and an image after noise reduction are substantially identical to each other (hereinafter, referred to as an image constraint condition before and after noise reduction), that is, a constraint condition for preventing the image from being too far from the original image, a constraint condition that noise of an image obtained by mapping an image to a sparse space substantially equals to zero (hereinafter, referred to as a sparse space constraint condition), a constraint condition that noise of a spatial differential value image of a separated image used for noise reduction of a Total Variation (TV) method substantially equals to zero (hereinafter, referred to as a spatial differential value constraint condition), and other constraint conditions are added to perform minimization processing with a regularization term. For these constraint conditions, the SNR spatial distribution calculated by the SNR distribution calculation unit 250 is used as a weight to perform the iterative computation.

For example, minimization processing expressed by Equation (7) is performed.

$$\hat{x} = \arg\min_{x} [f(x)]$$
$$= \arg\min_{x} [\lambda_1 \|W_{cons}(y-x)\|_2^2 + \lambda_2 W_{rglr} \|\Psi x\|_1] \quad (7)$$

In Equation (7), a first term represents the image constraint condition before and after noise reduction, and a second term represents the sparse space constraint condition, y represents an image before noise reduction, x represents an image after noise reduction, λ1 and λ2 represent a regularization parameter of the first term and a regularization parameter of the second term respectively, and Ψ represents a wavelet transform operator. Further, $W_{cons}$ and $W_{rglr}$ are weight images of the first and second terms, and the present embodiment uses, for example, the reciprocal "1/SNR" of the SNR spatial distribution obtained in S54 as a weight image $W_{rglr}$ of the second term.

In this manner, it is possible to increase weights of these constraint conditions for an image having a low SNR, to reduce weights of these constraint conditions for an image having a high SNR, to prevent excessive noise, and to improve accuracy of noise processing by adding the SNR as a weight to the constraint conditions other than the image constraint condition before and after noise reduction (sparse space constraint condition here).

In Equation (7), the sparse space constraint condition is exemplified as a constraint condition other than the image constraint condition before and after noise reduction, and the spatial differential value constraint condition may be used instead of or in combination with the sparse space constraint condition. Further, regarding noise correlation constraint condition disclosed in Japanese Patent No. 6762284, that is, an image before synthesis in the PI method (hereinafter, referred to as a pre-separation image), a constraint condition in which there is noise correlation between the pre-separation image and the post-separation image serves as constraint may be used, and an SNR (reciprocal thereof) can be used as a weight for these constraint conditions.

As described above, according to the present embodiment, the noise level is estimated (calculated) based on the image to be processed, the SNR spatial distribution is calculated using the spatial distribution of the noise level and signal distribution calculated based on the noise level, and the calculated SNR spatial distribution is used for adjustment of the constraint conditions in the noise reduction processing. As a result, it is possible to perform appropriate noise processing even for images having different noise levels and signal levels depending on the imaging conditions.

According to the present embodiment, it is possible to solve difficulty of noise reduction in the PI method in which a noise amount spatially changes before and after synthesis and thereby the SNR changes by applying the present embodiment to the image after synthesis in the PI method. However, the present embodiment may also be applied to an image before synthesis. In this case, the noise reduction processing may be omitted for the image after synthesis, and the noise reduction may be further performed on the image after synthesis.

Further, it is difficult to reduce noise without any signal loss due to a fact that the signal spatially changes (shading) when received by a plurality of coils. However, since the noise is reduced based on the SNR that reflects the spatial distribution of a signal, the noise can be reduced without any loss even at a location having a weak signal level.

In the present embodiment, the noise reduction unit 260 performs the minimization processing with the regularization term to reduce noise. Alternatively, it is also possible to use a noise reduction model learned to calculate an image in which noise is reduced from an image having different noise levels by using deep learning such as a convolutional neural network (CNN).

In this case, for example, it is possible to use the SNR distribution to spatially switch between a network learned with an image having a low SNR and a network having a high SNR so as to reduce noise.

Second Embodiment

A flow of basic processing according to the present embodiment is the same as flows shown in FIGS. 5 and 7. The present embodiment has a feature that noise level calculation is performed except a background region having low signal values in the noise level calculation processing (S52) of FIG. 5, and thus accuracy of the noise level calculation processing is improved.

Hereinafter, processing according to the present embodiment will be described with reference to FIG. 8.

First, similarly to S521 of FIG. 7, the absolute value image is multiplied by the reciprocal of the g factor to create the histogram (S5201). Next, similarly to S522 to S528 in FIG. 7, the maximum likelihood estimated value σ̂ is calculated based on estimation of the Rayleigh distribution (S5202). Next, a mask in which a region larger than the threshold Thre when the σ̂ is obtained is set to 0 and a region equal to or smaller than the threshold Thre is set to 1 is calculated (S5203), and a noise region (region of image space) is calculated using the mask (S5204).

Next, a spatial differential is calculated for the complex image in the noise region by the following Equation (8)

(S5205). Here, when a pixel value of a coordinate xn is I(xn) and a coordinate of an adjacent pixel is xn+1, a spatial differential ΔI(xn) is expressed by the following equation.

$$\Delta I(xn) = I(xn+1) - I(xn) \quad (8)$$

By performing spatial differentiation, only noise is extracted as a difference between adjacent pixels. Next, data after spatial differentiation is multiplied by the mask (S5206). As a result, an image with only noise is obtained in most cases. The histogram of the absolute value image is further calculated for this image, and the maximum likelihood estimated value σhat is calculated similarly to S5202 (S5207). The maximum likelihood estimated value σhat is multiplied by $\sqrt{2}$ to obtain the noise level of the complex noise (noise SD).

Thereafter, similarly to the first embodiment, the spatial distribution of the noise level is calculated using the noise SD, the signal distribution is calculated, the SNR spatial distribution is acquired (FIG. 5: S54), and the noise reduction processing is further performed using the SNR spatial distribution (FIG. 3: S304).

According to the present embodiment, noise in the background region of the image can be excluded from the target of reduction processing by using the mask, and the noise level is calculated by extracting only the noise by performing spatial differentiation on the region in which the noise should be processed, and thus the noise level can be calculated with higher accuracy.

Figure 8:
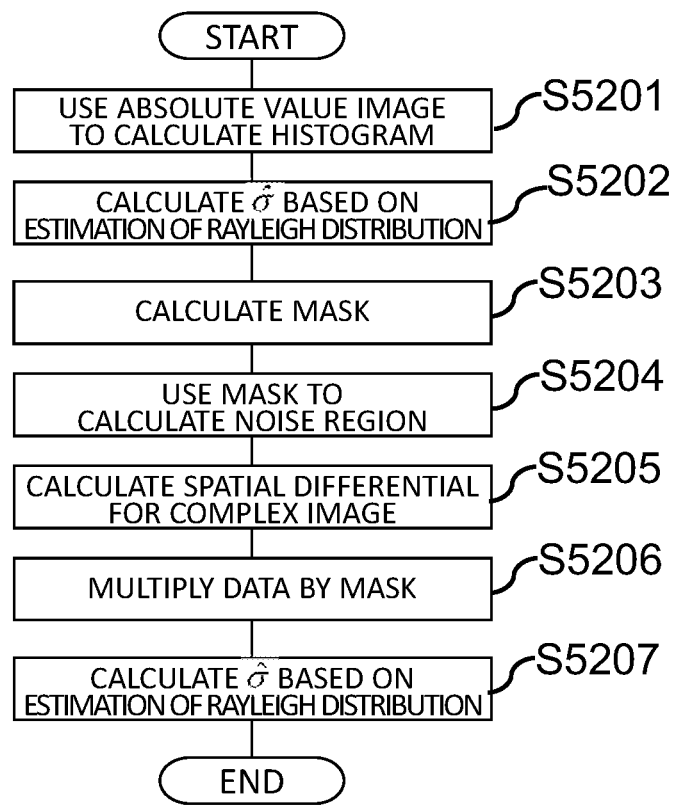
FIG. 8 is a diagram showing a flow of noise processing according to a second embodiment.

In a flow of FIG. 8, the noise level (noise SD) is calculated by performing spatial differentiation on the noise region estimated from the absolute value image, and it is also possible to use the absolute value image of the complex image subjected to the spatial differentiation as the absolute value image used for creating the histogram.

Verification Examples of First and Second Embodiments

Noise reducing methods (noise level estimation methods) according to the first and second embodiments are evaluated using a Shepp-logan numerical phantom. Results are shown in FIGS. 9A to 9C and FIGS. 10A to 10C. Upper diagrams of FIGS. 9A to 9C are histograms of all pixels, and lower diagrams show matching degrees between the Rayleigh distribution estimated by the method according to the first embodiment and the histogram. FIGS. 9A to 9C respectively show a case of SNR=5 (set noise SD=0.20000), a case of SNR=3.3 (set noise SD=0.30000), and a case of SNR=2.5 (set noise SD=0.40000).

The noise SD estimated based on the Rayleigh distribution estimated by the method according to the first embodiment is 0.20005, 0.29803, and 0.40050 in FIGS. 9A to 9C respectively, and thus it is confirmed that the noise SD well matches the set noise SD. However, it is confirmed that an error between the estimated Rayleigh distribution and the histogram increases as the SNR decreases.

Figure 10A:
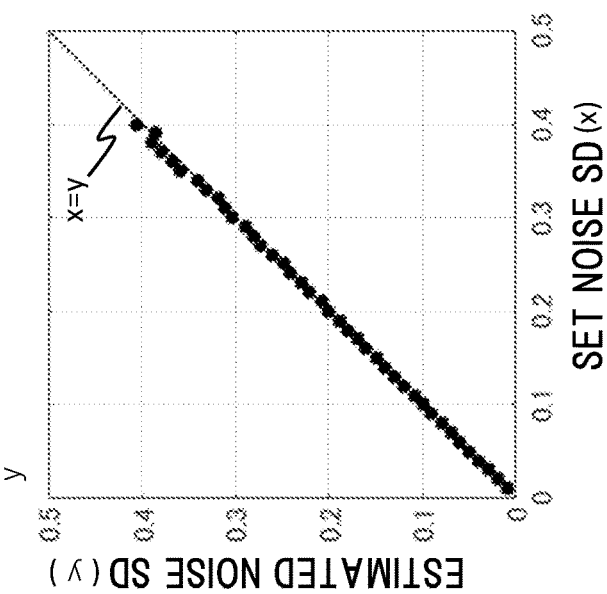
FIGS. 10A to 10C are diagrams showing effects of the first and second embodiments.
Figure 10B:
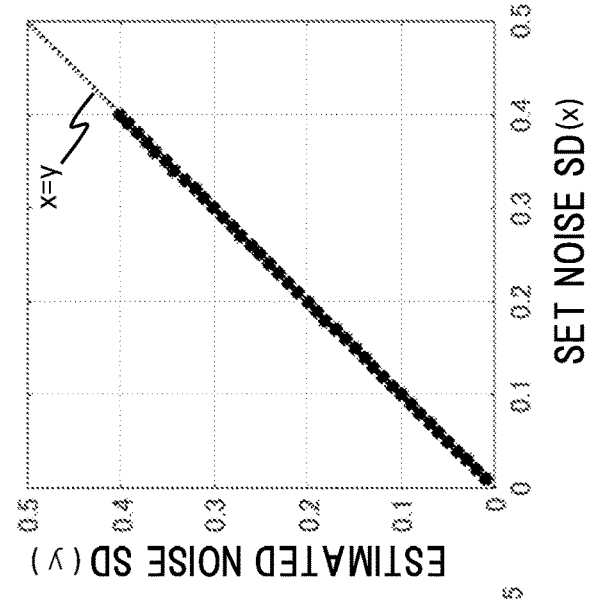
Figure 10C:
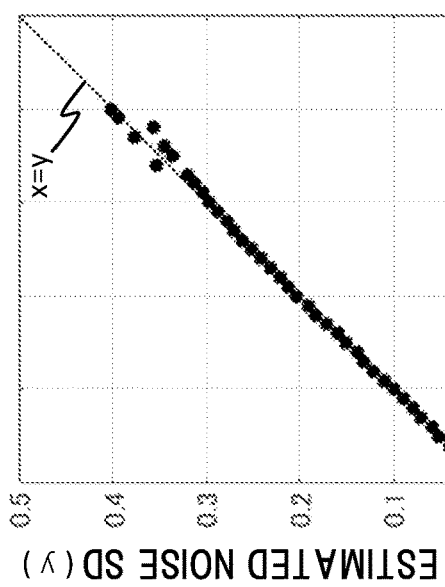

FIG. 10 is a diagram showing a relationship between the estimated noise SD and the set noise SD when using different noise estimation methods, and it is confirmed that the error is reduced to be small when the noise SD is 0.33 or less (i.e., SNR=3 or more) in a case of FIG. 10A using the method (calculation from the absolute value image) according to the first embodiment. As compared with the case of FIG. 10A, it is confirmed that accuracy in a case of FIG. 10B is improved in which the calculation is performed using the absolute value image obtained by performing spatial differentiation (only in the X direction) of the complex image. As compared with the case of FIG. 10A, it is also confirmed that accuracy in a case of FIG. 10C is improved using the method according to the second embodiment (noise SD is calculated by performing spatial differentiation after the noise SD is roughly estimated from the absolute value image).

Regarding two types of human head images with different imaging methods, the noise level is similarly estimated by the methods according to the first and second embodiments, and the same result is obtained. In particular, according to the method of the second embodiment, even in an image having a low SNR, a result having a high matching degree with the noise SD estimated from the noise SD of a MAC-synthesized image is obtained.

Display Embodiment

Figure 11:
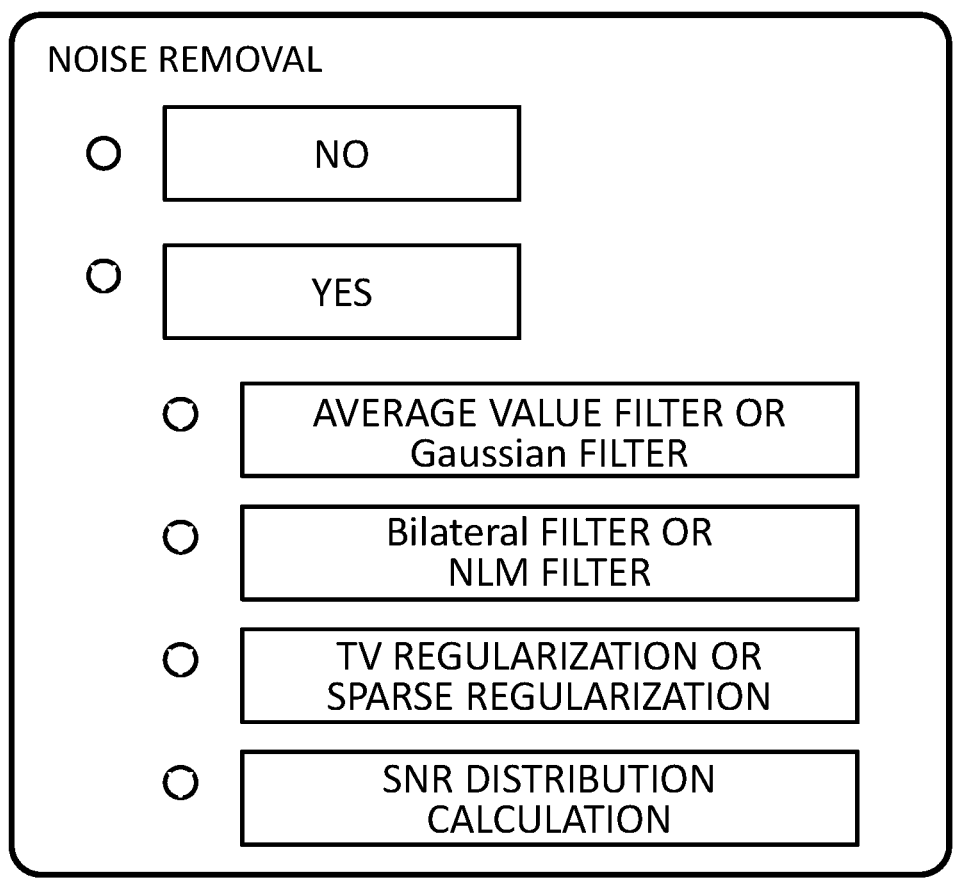
FIG. 11 is a diagram showing a display example.

The noise processing according to the first and second embodiments may be set as default processing in the image processing unit. Alternatively, when the imaging conditions are received via the input device 205, it is also possible to receive user selection with respect to the noise reducing method. In this case, for example, the display control unit 270 displays a UI as shown in FIG. 11 on the display 201. In the illustrated example, known noise reduction methods, for example, a linear filter such as an average value filter or a Gaussian filter, an edge preserving filter such as a bilateral filter, a nonlinear filter including total variation regularization or sparse regularization, and the noise reduction method according to the present embodiment can be selected. As a result, flexibility of method selection by the user increases.

What is claimed is:

1. A magnetic resonance imaging apparatus comprising:
   a measurement unit configured to receive a nuclear magnetic resonance signal generated in a subject by a receiving coil;
   an image reconstruction unit configured to process the nuclear magnetic resonance signal received by the receiving coil and reconstruct an image of the subject;
   an SNR spatial distribution calculation unit configured to calculate spatial distribution of noise of the image, calculate spatial distribution of the signal of the image, and calculate spatial distribution of a signal-to-noise ratio of the image using the spatial distribution of noise and the spatial distribution of the signal of the image;
   a noise reduction unit configured to perform noise reduction to reduce noise from the image based on the spatial distribution of the signal-to-noise ratio; and
   a noise processing unit configured to cause a reduced-noise image to be output, based on the noise reduction by the noise reduction unit.

2. The magnetic resonance imaging apparatus according to claim 1, wherein
   the measurement unit includes a plurality of receiving coils, and the image reconstruction unit synthesizes nuclear magnetic resonance signals received by the plurality of receiving coils respectively or images reconstructed from the nuclear magnetic resonance signals to reconstruct an image, and
   the SNR spatial distribution calculation unit calculates the spatial distribution of the signal-to-noise ratio for an image obtained after synthesis by the image reconstruction unit.

3. The magnetic resonance imaging apparatus according to claim 2, wherein
   the image reconstruction unit synthesizes the nuclear magnetic resonance signals received by the receiving coils using parallel imaging computation or images reconstructed from the nuclear magnetic resonance signals.

4. The magnetic resonance imaging apparatus according to claim 1, wherein
the SNR spatial distribution calculation unit includes:
a noise level calculation unit configured to calculate a noise level of the image,
a noise distribution calculation unit configured to calculate spatial distribution of noise of the image, and
a signal distribution calculation unit configured to calculate spatial distribution of the signal of the image, and
the spatial distribution of the signal-to-noise ratio is calculated using the noise level, the spatial distribution of noise, and the spatial distribution of the signal.

5. The magnetic resonance imaging apparatus according to claim 4, wherein
the noise level calculation unit calculates the noise level based on a histogram of an absolute value of the image.

6. The magnetic resonance imaging apparatus according to claim 5, wherein
the noise level calculation unit further calculates the noise level based on the histogram of the absolute value of a spatial differential of the image.

7. The magnetic resonance imaging apparatus according to claim 4, wherein
the measurement unit includes a plurality of receiving coils, and
the noise distribution calculation unit calculates noise distribution using a g factor of each receiving coil.

8. The magnetic resonance imaging apparatus according to claim 1, wherein
the noise reduction unit reduces noise by error minimization computation using a plurality of constraint conditions, and uses the spatial distribution of the signal-to-noise ratio as a weight of the constraint conditions.

9. The magnetic resonance imaging apparatus according to claim 8, wherein
the plurality of constraint conditions include an image constraint condition before and after noise reduction in which an image before noise reduction and an image after noise reduction are substantially identical to each other, a sparse space constraint condition in which noise of an image obtained by mapping the image after noise reduction to sparse space substantially equals to zero, and/or a spatial differential value constraint condition in which noise of a spatial differential value image of the image before noise reduction substantially equals to zero, and
the noise reduction unit uses the spatial distribution of the signal-to-noise ratio as a weight of a constraint condition other than the image constraint condition before and after noise reduction.

10. The magnetic resonance imaging apparatus according to claim 1, wherein
the noise reduction unit includes a machine learning model learned to output an image after noise reduction from an image having different noise levels, and adjusts a coefficient of the machine learning model based on the spatial distribution of the signal-to-noise ratio.

11. A noise reduction method for reducing noise from an image acquired by a medical imaging apparatus, the noise reduction method comprising steps of:
(a) calculating spatial distribution of the noise of the image, calculating spatial distribution of a signal, acquired by the medical imaging apparatus, of the image, and calculating spatial distribution of a signal-to-noise ratio of the spatial distribution of the noise of the image and the spatial distribution of the signal of the image;
(b) performing noise reduction to reduce noise from the image based on the spatial distribution of the signal-to-noise ratio; and
(c) causing a reduced-noise image to be output, based on the noise reduction in (b).

12. The noise reduction method according to claim 11, wherein
the image is obtained by synthesizing nuclear magnetic resonance signals received by a plurality of receiving coils of a magnetic resonance imaging apparatus respectively, or images reconstructed from the nuclear magnetic resonance signals, and
the spatial distribution of the noise is calculated using g factors of the plurality of receiving coils.

13. The noise reduction method according to claim 11, further comprising
calculating a noise level based on a histogram of an absolute value image calculated from the image.

14. The noise reduction method according to claim 11, further comprising
calculating a spatial differential of the image; and extracting a noise region, wherein
a noise level is calculated from the noise region.

15. An image processing apparatus for reducing noise from an image based on a signal acquired by a medical imaging apparatus, the image processing apparatus comprising:
an SNR spatial distribution calculation unit configured to calculate spatial distribution of the noise of the image, calculate spatial distribution of the signal of the image, and calculate spatial distribution of a signal-to-noise ratio of the image using the spatial distribution of the noise and the spatial distribution of the signal of the image;
a noise reduction unit configured to perform noise reduction to reduce noise from the image based on the spatial distribution of the signal-to-noise ratio; and
a noise processing unit configured to cause a reduced-noise image to be output, based on the noise reduction by the noise reduction unit.

16. The image processing apparatus according to claim 15, wherein
the SNR spatial distribution calculation unit includes:
a noise level calculation unit configured to calculate a noise level of the image,
a noise distribution calculation unit configured to calculate the spatial distribution of the noise of the image, and
a signal distribution calculation unit configured to calculate the spatial distribution of the signal of the image, and
the spatial distribution of the signal-to-noise ratio is calculated using the noise level, the spatial distribution of the noise, and the spatial distribution of the signal.

17. The image processing apparatus according to claim 15, wherein
the noise reduction unit reduces noise by error minimization computation using a plurality of constraint conditions, and uses the spatial distribution of the signal-to-noise ratio as a weight of the constraint conditions.

18. The image processing apparatus according to claim 15, wherein the noise reduction unit includes a machine learning model learned to output an image after noise reduction from an image having different noise levels, and adjusts a coefficient of the machine learning model based on the spatial distribution of the signal-to-noise ratio.

* * * * *